United States Patent [19]
Nordan

[11] Patent Number: 6,152,958
[45] Date of Patent: Nov. 28, 2000

[54] FOLDABLE THIN INTRAOCULAR MEMBRANE

[76] Inventor: Lee T. Nordan, 9834 Genesee Ave., Suite 209, La Jolla, Calif. 92037

[21] Appl. No.: 09/215,574

[22] Filed: Dec. 16, 1998

[51] Int. Cl.[7] ........................................................ A61F 2/16
[52] U.S. Cl. .......................................... 623/6.25; 623/6.43
[58] Field of Search ............................... 623/6, 6.18–6.21, 623/6.25

[56] References Cited

U.S. PATENT DOCUMENTS

| | | |
|---|---|---|
| 4,215,440 | 8/1980 | Worst . |
| 4,370,760 | 2/1983 | Kelman . |
| 4,704,122 | 11/1987 | Portnoy ........................................ 623/6 |
| 4,828,558 | 5/1989 | Kelman . |
| 4,863,465 | 9/1989 | Kelman . |
| 4,932,970 | 6/1990 | Portney ........................................ 623/6 |
| 4,950,288 | 8/1990 | Kelman . |
| 5,071,432 | 12/1991 | Baikoff . |
| 5,192,319 | 3/1993 | Worst . |
| 5,300,117 | 4/1994 | Baikoff et al. . |
| 5,476,515 | 12/1995 | Kelman et al. . |
| 5,769,889 | 6/1998 | Kelman . |
| 5,776,191 | 7/1998 | Mazzocco ................................... 623/6 |

*Primary Examiner*—David H. Willse
*Attorney, Agent, or Firm*—Henri J. A. Charmasson; John D. Buchaca

[57] ABSTRACT

A thin foldable intraocular implant specifically configured for installation into the anterior chamber of a phakic or pseudophakic eye has broad positioning flaps that do not apply any substantial pressure against the wall of the eye. It can be rolled for insertion through a corneal incision as small as 2.75 millimeters. The implant is constituted by a resiliently flexible membrane, with an overall thickness as low as 10 microns, that vaults the iris without contacting it.

8 Claims, 2 Drawing Sheets

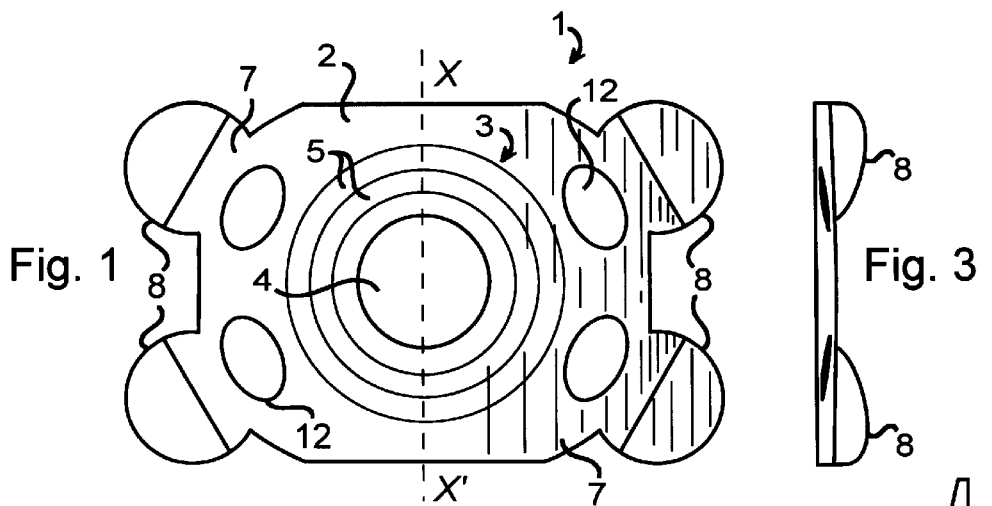
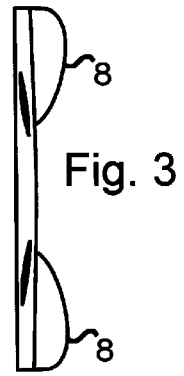
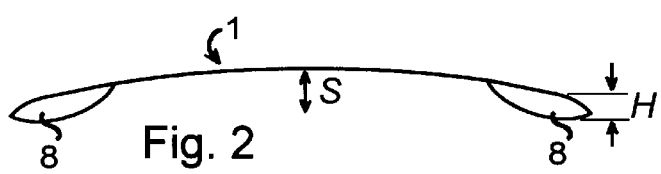
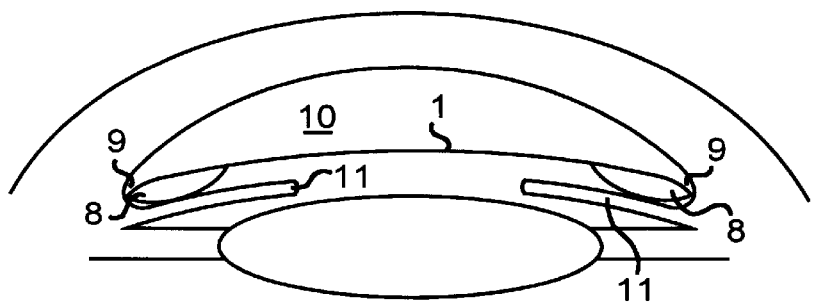
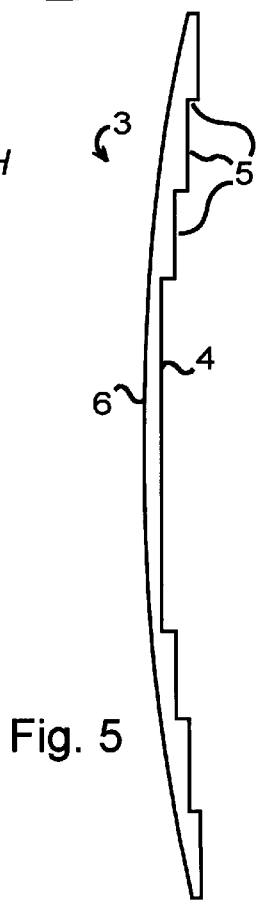

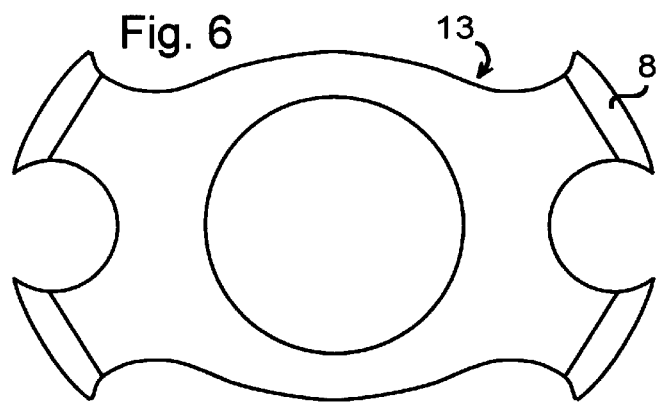
Fig. 6
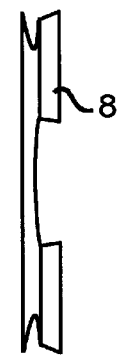
Fig. 8
Fig. 7
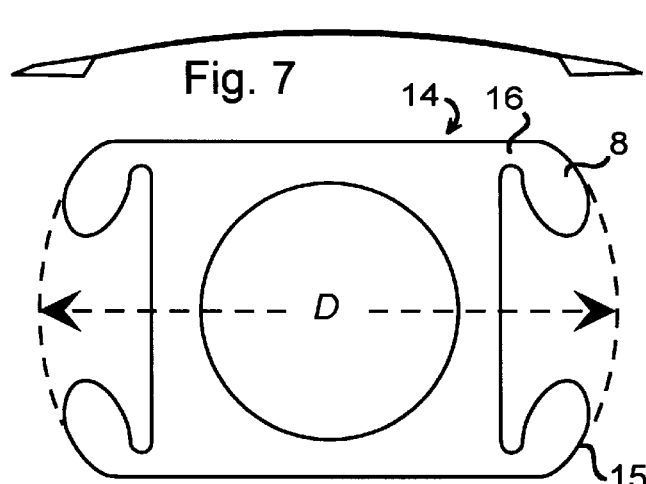
Fig. 9
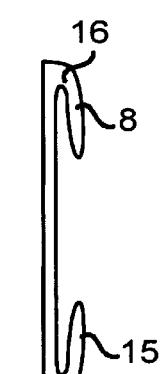
Fig. 11
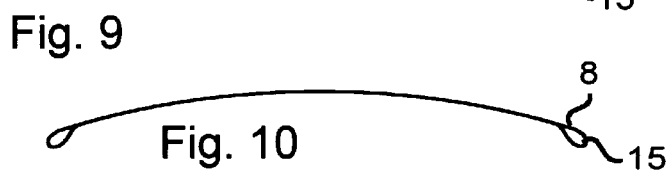
Fig. 10
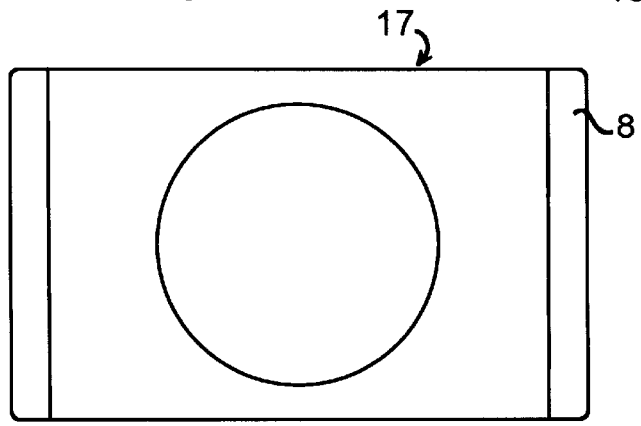
Fig. 12
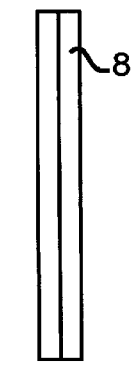
Fig. 14
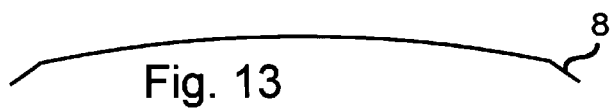
Fig. 13

FOLDABLE THIN INTRAOCULAR MEMBRANE

FIELD OF THE INVENTION

The present invention relates to intraocular implants, and more specifically to implants intended to be inserted in the anterior chamber of the eye in order to correct optical deficiencies without removal of the crystalline lens.

BACKGROUND OF THE INVENTION

Intraocular lenses (IOLs) are routinely used nowadays for restoring vision after removal of the cataracted lens. Whether the IOL is installed in the posterior chamber of the eye in lieu of the removed cataracted lens, or in the anterior chamber, it must be small enough to pass through a minimal corneal incision. The reduction in the overall dimension of the IOL is limited however, by the necessity of avoiding glare by providing a substitute optic that is large enough to cover the pupil when it is fully dilated for proper night time vision. One approach to reducing glare while at the same time reducing the size of the incision in the cornea is to construct the IOL from several pieces which are joined together after the individual pieces are inserted through the corneal incision as disclosed in U.S. Pat. No. 5,769,889 Kelman. The complexity of this type of IOLs, the difficulty of their post insertion assembly coupled with the required thickness and rigidity of the optic element, still force the ophthalmic surgeon into tolerable compromises between reduced size and peripheral glare coupled with impaired night vision.

Conventional lenticular elements, whatever their size, are still subject to various spherical and thickness aberrations which are not easily correctable during the manufacture of the IOL.

The invention results from a search for a simple, preferably one-piece IOL with an optic having a diameter sufficient to cover the size of a dilated pupil, but yet insertable to a relatively small corneal incision.

SUMMARY OF THE INVENTION

The principal and secondary objects of this invention are to provide the ophthalmic surgeon with a simple, one-piece IOL which avoids the major drawbacks of the device of the prior art, particularly reduced coma, glare, impaired night vision, and blurring due to spherical and thickness aberrations, and which can be collapsed to a relatively small size for insertion through a corneal incision of about 2.75 millimeters.

These and other valuable objects are achieved by forming a thin lens inherently immune to spherical and thickness aberrations on a resiliently flexible membrane that can be rolled or folded to pass through a small corneal incision. The thin lens optic typically uses a small central lenticular zone surrounded by a plurality of optic rings concentric with the central zone and extends up to a total diameter of approximately 6 millimeters. The membrane and its incorporated thin lens optic is arcuately shaped for installation in the anterior chamber where it vaults the iris and is stabilized by sets of obliques flaps that nest into the corner of the chamber. Contrary to the compressed haptics commonly used to secure prior art, IOLs, the aforesaid flaps do not exert any pressure upon the wall of the eye. The vaulted shape of the device combined with its thinness keep it away from the endothelium. Its neutral buoyancy prevent any pressure on the iris eliminating risks of closure, cataract or iris pigment dispersion. The large footprint of the flaps prevent synechiae and their encapsulation by the iris. The natural buoyancy of the device is improved by a plurality of fenestrations. The thin lens can be configured in a variety of successive dioptic powers in order to correct practically all types of refractive errors.

BRIEF DESCRIPTION OF THE DRAWING

FIG. 1 is a front elevational view of the preferred embodiment of the invention;

FIG. 2 is a bottom plan view thereof;

FIG. 3 is a side elevational view thereof;

FIG. 4 is a diagrammatical illustration of the device implantation in the anterior chamber of the eye;

FIG. 5 is a cross-sectional view of a thin lens optic region;

FIG. 6 is a front elevational view of a first alternate embodiment of the invention;

FIG. 7 is a bottom plan view thereof;

FIG. 8 is a side elevational view thereof;

FIG. 9 is a front elevational view of a second alternate embodiment of the invention;

FIG. 10 is a bottom plan view thereof;

FIG. 11 is a side elevational view thereof;

FIG. 12 is a front elevational view of third alternate embodiment of the invention;

FIG. 13 is a bottom plan view thereof; and

FIG. 14 is a side elevational view thereof.

DESCRIPTION OF THE PREFERRED EMBODIMENT OF THE INVENTION

Referring now to the drawing, there is shown a refractively corrective device 1 shaped and dimensioned for installation in the anterior chamber of a phakic or pseudophakic eye. The device consists essentially of a membrane preferably made of flexible polymethylmethacrylate (PMMA). Other resilient materials such as silicone or hydrogel could also be used. The overall dimensions are approximately 12 millimeters in length, 8 millimeters in width and an overall thickness of approximately 10 to 100 microns. The membrane can be bent and even rolled or folded for insertion into the interior chamber through a small incision of no more than 2.75 millimeters in length. The membrane has enough resiliency to return to its prerolled or prefolded shape. The optic region 2 in the center of the membrane has an overall diameter of approximately 6 millimeters. The optic region is essentially constituted by what is called a "thin lens" in the fields of optics and ophthalmology. A thin lens is a refractive device of the type 3 illustrated in FIG. 4 that combines a lenticular central zone 4 with a plurality of refractive rings 5 surrounding and concentric with the lenticular zone 4. In some applications, the entire optical element may be constituted by concentric rings. Those concentric rings resemble the rings of a Fresnel lens, except that instead of defining a prism, each ring has a front surface 6 espousing a continuous curve in common with the front surface of the central lenticular zone 4. It should be noted that this curved front surface may be convex, or concave depending upon the type of correction required and is seldom spherical, but may exhibit various degrees of asphericity as required to provide both a single diopter correction or multi-diopter correction as previously taught in my U.S. Pat. No. 5,236,452 issued Nov. 21, 1991, which patent is incorporated in this specification through this reference. The optic is typically made by machining the PMMA membrane with a laser milling machine. The two lateral portions 7 of the membrane astride the median optic region 2 are shaped to define at least two flaps 8 which are permanently bent obliquely backward in relation to the median region in order to nest intimately into the corner 9 of the anterior chamber as illustrated in FIG. 4. Accordingly, the median portion and the lateral portion with their bent flaps 8 form a vault having a total sagital length S of approximately 1 millimeter whereby the membrane 1 spans the anterior chamber 10 in a direction substantially parallel to the iris 11. It should be noted that the median portion and the lateral portions exclusive of the flaps may be slightly arcuate about the transversal length central axis XX' to a total sagital length of approximately 0.5 millimeter. In which case, the height of the flaps H would be reduced to approximately 0.5 millimeter in order to obtain a total vault height or sagital length S of approximately 1 millimeter. The curvature of the membrane and the bent of flaps are permanently imparted during the fabrication of the device.

Alternate embodiments of the device are illustrated in FIGS. 6–14. In each of these alternate embodiments, the membrane returns to its arcuate shape and backward projecting flaps 9. Each device fits within a circle having a diameter D of approximately 13 millimeters. Due to the flexibility of the membrane, this size can accommodate practically all eye sizes.

In the embodiment 13 of FIGS. 6–8, the surface of the membrane is reduced for maximum buoyancy.

In the embodiment 14 of FIGS. 9–11, the flaps have an increased thickness along their edges 15 to create a larger footprint against the wall of the eye. The collar regions 16 between each flap and the main body of the membrane is thinned down to about 20 microns in order to provide flexibility with a modicum amount of resiliency.

The embodiment 17 of FIGS. 12–14 is of a simplified shape that can provide an even larger optic zone.

While the preferred embodiments of the invention have been described, modifications can be made and other embodiments may be devised without departing from the spirit of the invention and the scope of the appended claims.

What is claimed is:

1. A single piece corrective device for installation in the anterior chamber of a phakic or pseudophakic eye which comprises:
   a single thin, resiliently bendable membrane shaped and dimensioned to span the anterior chamber substantially parallelly to the iris;
   said membrane having a substantially constant thickness in a range of approximately 10 to 100 microns;
   said membrane comprising a corrective median portion, and at least two lateral portions astride said median portion wherein said corrective portion includes a thin lens;
   wherein said thin lens comprises a discontinuous optic zone having a plurality of concentric optic rings.

2. The device of claim 1, wherein said thin lens further includes a central continuous optic zone.

3. The device of claim 2, wherein said median portion and lateral portions form a vault having a sagittal length of approximately 1 millimeter.

4. The device of claim 1, wherein each of said lateral portions comprises at least one anchoring flap bent obliquely backward in relation to said median portion, and shaped and dimensioned to intimately nest into the corner of the anterior chamber.

5. The device of claim 1, wherein said membrane is made of flexible PMMA.

6. The device of claim 1, wherein said thin lens has correction powers in a range of approximately minus 15 diopters to plus 15 diopters.

7. A method for treating optical deficiency of a patient's eye which comprises:
   installing, in the anterior chamber of said eye, a one-piece, single component corrective device, said device comprising:
   a thin, resiliently bendable membrane shaped and dimensioned to arcuately span the anterior chamber substantially parallelly to the iris;
   said membrane having a substantially constant thickness in a range of approximately 10 to 100 microns, and comprising a corrective median portion, and at least two lateral portions astride said median portion wherein said corrective portion includes a thin lens having a discontinuous optic zone including a plurality of concentric optic rings.

8. The method of claim 7, wherein said step of installing further comprises making a corneal incision in said eye, of no more than 2.75 millimeters in length;
   curling said membrane; and
   inserting said membrane through said incision.

* * * * *